United States Patent
Reuter et al.

[11] Patent Number: 5,371,290
[45] Date of Patent: Dec. 6, 1994

[54] PREPARATION OF N,N-DIALKARYLAMINES

[75] Inventors: Peter Reuter, Mannheim; Willi A. Weber, Ludwigshafen; Hans Diem, Mannheim, all of Germany

[73] Assignee: BASF Aktiengesellschaft, Ludwigshafen, Germany

[21] Appl. No.: 189,294

[22] Filed: Jan. 31, 1994

Related U.S. Application Data

[63] Continuation of Ser. No. 983,420, Nov. 30, 1992, abandoned.

[30] Foreign Application Priority Data

Nov. 29, 1991 [DE] Germany ............... 4139362

[51] Int. Cl.$^5$ ............................ C07C 209/04
[52] U.S. Cl. .......................... 564/402; 564/401
[58] Field of Search ..................... 564/402, 401

[56] References Cited

U.S. PATENT DOCUMENTS

| | | | |
|---|---|---|---|
| 2,991,311 | 3/1961 | Thoma | 260/577 |
| 3,969,411 | 7/1976 | Schneider et al. | 260/577 |
| 4,150,054 | 1/1979 | Schneider | 260/577 |
| 5,113,018 | 5/1992 | Kurano | 564/403 |
| 5,159,115 | 10/1992 | Pappas | 564/401 |

FOREIGN PATENT DOCUMENTS

| | | |
|---|---|---|
| 1031796 | 5/1958 | Germany. |
| 2348738 | 10/1975 | Germany. |
| 2658728 | 11/1978 | Germany. |
| 287489 | 10/1983 | Germany. |

OTHER PUBLICATIONS

Chemical Abstracts, vol. 115, abstract No. 31575p (Nov. 1991).
Houben-Weyl, Methoden Der Organischen Chemie, vol. XI/I, (1991) pp. 134–143, Stuttgart 1957.
European Search Report, EP92/119691 (Apr. 1993).

*Primary Examiner*—Richard L. Raymond
*Assistant Examiner*—B. Burn
*Attorney, Agent, or Firm*—John H. Shurtleff

[57] ABSTRACT

A process for the preparation of N,N-dialkylarylamines (I) by reacting arylamines (II) with alcohols (IIIa) or dialkyl ethers (IIIb) in the presence of an oxygen acid of phosphorus or in the presence of an ammonium salt thereof as catalyst, comprises reacting the oxygen acid of phosphorus with an arylamine (IV) before the reaction is commenced. The invention also relates to the regeneration of the catalyst by occasionally interrupting the reaction and treating the catalyst phase at from 100° to 300° C. with steam or water.

6 Claims, No Drawings

PREPARATION OF N,N-DIALKARYLAMINES

This application is a continuation of application Ser. No. 07/983,420, filed Nov. 30, 1992 (now abandoned).

The present invention relates to an improved process for the preparation of N,N-dialkylarylamines (I) by reacting arylamines (II) with alcohols (IIIa) or dialkyl ethers (IIIb) in the presence of an oxygen acid of phosphorus or in the presence of an ammonium salt thereof as catalyst.

The present invention furthermore relates to the regeneration of the catalyst during the preparation of (I) from (II) and (IIIa) or (IIIb).

As is known, N,N-dialkylarylamines are valuable intermediates for the preparation of crop-protection agents and other biological active compounds such as growth regulators. In addition, they are used as starting materials for the synthesis of pharmaceuticals and dyes, in particular azo dyes, and as additives for paints and mineral oils.

DE-B 1 031 796 discloses passing a mixture of an aromatic amine and an alcohol through hot, concentrated phosphoric acid in order to N-alkylate aniline in the liquid phase. The disadvantage of this process is that, in addition to the N,N-dialkyl compounds, considerable amounts of N-monoalkyl compounds are always produced as undesired by-products. Further disadvantages are that, after an extended operating time, the catalytic activity of the phosphoric acid drops, the conversions are reduced and ring alkylation occurs as a side reaction.

DE-A 2 658 628 describes the N-alkylation of aromatic amines in the presence of heated phosphoric acid to which an aliphatic amine or a phosphoric acid salt or quaternary ammonia salt of the amine is added before or after commencement of the reaction. The phosphoric acid may also be replaced by metaphosphoric acid or a poly-phosphoric acid. The activity is adversely affected by the alkylation of the aliphatic amine, which occurs in an undesired side reaction, and the inhomogeneous distribution of the salts in the catalyst phase.

It is an object of the present invention to overcome the abovementioned disadvantages and to provide a selective, virtually by-product-free process for the preparation of N,N-dialkylarylamines (I). It is a further object of the present invention to regenerate the catalyst for the preparation of N,N-dialkylarylamines (I), i.e. to restore its original activity and productivity as far as possible, in a simple and economical manner.

We have found that this object is achieved by an improved process for the preparation of N,N-dialkylarylamines (I) by reacting arylamines (II) with alcohols (IIIa) or dialkyl ethers (IIIb) in the presence of an oxygen acid of phosphorus or in the presence of an ammonium salt thereof as catalyst, which comprises reacting the oxygen acid of phosphorus with an arylamine (IV) before the reaction is commenced.

We have furthermore found that this object is achieved by a process for the preparation of N,N-dialkylarylamines (I) by reacting arylamines (II) with alcohols (IIIa) or dialkyl ethers (IIIb) in the presence of an oxygen acid of phosphorus or in the presence of an ammonium salt thereof as catalyst, which comprises occasionally interrupting the reaction and treating the catalyst phase at from 100° to 300° C. with steam or water.

Suitable arylamines (IV) are in particular N,N-dialkylarylamines (I), i.e. the alkylation products of the starting arylamines (II). The starting arylamines (II) are also suitable for preparing the catalyst. Although other arylamines may also be suitable, they must, as substances which are foreign to the synthesis, be purified in additional process steps.

Suitable amines (IV) for the preparation of N,N-dimethylaniline from aniline and methanol are therefore in particular N,N-dimethylaniline and aniline.

In general, the preferred amine (IV) has the formula (IVa)

where
Ar is aryl, such as phenyl or naphthyl, and
$R^1$ and $R^2$ are hydrogen or $C_1$–$C_{10}$-alkyl, preferably $C_1$–$C_6$-alkyl.

Ar may carry one or more substituents, for example alkyl, alkoxy or halogen.

Suitable oxygen acids of phosphorus which are pretreated with the amine (IV) are orthophosphoric acid and in particular the anhydro acids of orthophosphoric acid, such as, in particular, metaphosphoric acid. In general, the condensation of the oxygen acid of phosphorus and the attendant elimination of water is carried out at from 120° to 270° C., preferably at from 160° to 230° C., in particular at from 200° to 210° C.

The reaction of the oxygen acid of phosphorus is expediently carried out with gaseous arylamine (IV) which has previously been evaporated outside the reactor, and gives an active catalyst phase which has low volatility under the reaction conditions and whose molar ratio between the arylamine (IV) and the phosphorus content of the oxygen acid of phosphorus is from 0.1:1 to 2:1, preferably from 0.3:1 to 1.5:1. It is also possible to pass the arylamine (IV) through the oxygen acid until the absorption capacity of the latter is exhausted and the arylamine can be detected as a gas in the product from the reactor.

The same applies to the ammonium salts of the oxygen acids o f phosphorus.

After the catalyst has been prepared in accordance with the invention, the subsequent alkylation of the arylamine (II) is carried out in a conventional manner by passing the arylamine (II) and the alcohol (IIIa) or the dialkyl ether (IIIb) in gas form through the catalyst phase. It is possible first to heat the two starting components to the desired reaction temperature outside the reactor. The gaseous product mixture leaving the reactor is worked up in a conventional manner. After the condensation and removal of unreacted gaseous starting materials, which can be recycled into the reaction, the liquid product mixture is separated into an aqueous phase and a phase containing the crude product. The crude product phase can be worked up further in a fractionating column.

The process is of particular importance for the N,N-dialkylation of aniline and ring-substituted derivatives thereof. Possible substituents of aniline are halogens, such as fluorine, chlorine and bromine, and $C_1$–$C_6$-alkyl, $C_1$–$C_6$-alkoxy, nitro and cyano groups. It is also possible for more than one of these substituents to be present.

Particularly preferred starting materials are aniline, o-, m- and p-toluidine, the xylidenes and anisidines, and halogen-substituted anilines.

The alcohols (IIIa) used are preferably straight-chain or branched $C_1$–$C_{10}$-alkanols; methanol and ethanol are particularly suitable. Alkenols, cycloalkanols and aralipatic alcohols, such as benzyl alcohol, are also suitable.

The dialkyl ethers (IIIb) used are ethers containing alkyl radicals having 1 to 6 carbon atoms, particular preference being given to ethers containing identical alkyl radicals. Dimethyl ether and diethyl ether are particularly important.

In general, the alcohol (IIIa) or the dialkyl ether (IIIb) are employed in excess over the stoichiometrically necessary amount. Advantageously from 1 to 10 mol, particularly from 1 to 4 mol, of alkylating agent are preferably employed per mol of arylamine (II). The unreacted, excess alcohol or dialkyl ether can be recovered and recycled after any water present therein due to the reaction has been removed.

The amount of catalyst built up from the oxygen acid of phosphorus and arylamine (IV) is not crucial, but is preferably at least 0.01 kg, in particular from 0.05 to 0.1 kg, per kg of arylamine (II) reacted per hour. In general, larger amounts have no further advantages.

The alkylation of the arylamine (II) is carried out at from 180° to 250° C., preferably at from 200° to 230° C. At temperatures below 180° C. the reaction slows excessively or the starting materials, depending on which are selected, are no longer in gaseous form. Above 250° C. ring-alkylation reactions can be expected.

The reaction is carried out at from slightly superatmospheric pressure to about 2 bar. If desired, the reaction can also be carried out at atmospheric pressure.

The catalyst preparation according to the invention has the advantage over the prior art that the formation of by-products, in particular N-monoalkylarylamines, due to reaction of the oxygen acid of phosphorus with an arylamine (IV) before commencement of the alkylation reaction is reduced. An additional drop in the proportion of by-products occurs in the reaction with the N,N-dialkylarylamine (I) which can be prepared by the process. This is particularly advantageous since distillative work-up is significantly simplified or can be omitted entirely.

In the preparation of N,N-dimethylaniline, pretreatment of the oxygen acid of phosphorus with aniline or N,N-dimethylaniline increases the selectivity. Treatment with N,N-dimethylaniline furthermore causes a constant composition in the crude product phase to be established at a very early stage.

Independently of the catalyst preparation according to the invention by pretreatment of the oxygen acid of phosphorus with an arylamine (IV), it has proven extremely advantageous occasionally to interrupt the reaction in order to treat the catalyst phase with steam or water at from 100° to 300° C., preferably at from 150° to 300° C., in particular at from 180° to 250° C.

The time for which the steam or water is passed in is generally from 0.1 to 3 hours, preferably from 0.3 to 3 hours, particularly preferably from 0.5 to 2 hours. It has furthermore proven expedient to pass from 0.1 to 400 kg, preferably from 1 to 300 kg, in particular from 10 to 200 kg, of steam through the catalyst phase per $m^3$ of catalyst per hour. The steam can also be replaced by water.

After the steam treatment, nitrogen can be passed through the catalyst phase in order to expel excess water which has not been taken up by the catalyst. This measure is not absolutely necessary, since the water can also be removed from the reactor with the product stream by recommencing the synthesis.

The regeneration process according to the invention has the advantage over the prior art that the productivity of the catalyst is retained due to the treatment with steam or water and the throughput of starting materials need not be reduced. The occasional introduction of steam presumably causes readily volatile organophosphorus compounds, formed by reaction of the catalyst with the starting materials, to be hydrolyzed, re-forming the oxygen acid of phosphorus.

Preliminary experiments had showed that, after an operating time of more than 2 months, readily volatile organophosphorus substances are entrained with the gaseous reactor product, causing considerable corrosion in the downstream apparatus and consequently increased production costs.

N,N-Dialkylarylamines (I) prepared by the processes according to the invention are valuable intermediates for organic syntheses, including for the preparation of crop-protection agents, drugs and dyes.

The catalyst preparation and regeneration processes according to the invention are of particular importance for the preparation of N,N-dimethylaniline from aniline and methanol and for the preparation of N,N-diethylaniline from aniline and ethanol.

EXAMPLES 1 TO 5

Preparation of N,N-dimethylaniline

A cylindrical reactor with a capacity of 3 $m^3$, which had been charged with 1 $m^3$ of orthophosphoric acid, was heated to 210° C. Water of condensation consequently liberated from the orthophosphoric acid was removed from the reactor by means of a stream of nitrogen. Gaseous aniline or gaseous N,N-dimethylaniline was subsequently passed into the resultant oxygen acid of phosphorus until the molar nitrogen:phosphorus ratio shown in the table had been reached in each case. A gaseous mixture of 130 kg of aniline and 177 kg of methanol (molar ratio 1:4) was then passed through the reactor per hour at 228° C., with a residence time of the starting materials of 50 seconds in each case.

The reactor product was condensed, and unreacted methanol was removed by distillation. After the aqueous phase in the still had been separated off, the phase containing the crude product was analyzed by gas chromatography.

EXAMPLE 6

Preparation of N,N-diethylaniline

The procedure was similar to that of Examples 1 to 5, but the mixture of aniline and methanol was replaced by a gaseous mixture of 100 kg of aniline and 195 kg of ethanol (molar ratio 1:4).

EXAMPLE 7

(comparative example)

The procedure was similar to that of Examples 1 to 5, but the oxygen acid of phosphorus was not reacted with the arylamine.

The results of Examples 1 to 7 are shown in the table.

They show that, compared with the prior art, treatment of the oxygen acid of phosphorus with arylamine (IV), in particular with N,N-dimethylaniline, increases the selectivity in the preparation of N,N-dimethylaniline by the novel process and reduces the proportion of by-products in the crude product, in particular the proportion of N-monomethylaniline.

EXAMPLE 8

A cylindrical reactor with a capacity of 3 m$^3$, which had been charged with 1 m$^3$ of orthophosphoric acid, was heated to 230° C. Water of condensation consequently liberated from the orthophosphoric acid was removed from the reactor by a stream of nitrogen. Gaseous aniline was subsequently passed through the resultant oxygen acid of phosphorus until it was no longer taken up and was detectable in the product from the reactor. A gaseous mixture of 130 kg of aniline and 177 kg of methanol (molar ratio 1:4) was then passed through the reactor per hour. The reactor product was condensed, and unreacted methanol was removed by distillation. After the aqueous phase present in the still had been separated off, the phase containing the crude product was fed to a fractionating column.

Analysis of the crude product and the distilled product by gas chromatography gave the following results:

98.55% by weight of N,N-dimethylaniline,
0.95% by weight of N-monomethylaniline,
0.5% by weight of o- and p-toluidines and
0.001% by weight of aniline.

The distilled product contained 99.8% by weight of N,N-dimethylaniline.

Over the course of 60 days, the productivity dropped by 50% due to deactivation of the catalyst phase, so that the throughput of aniline and methanol had to be reduced to 65 kg/h and 88 kg/h respectively. The reaction was interrupted and the feed of the starting materials stopped to allow 50 kg of steam to be passed through the catalyst for 2 hours at 230° C. and 4 bar.

This restored the original activity of the catalyst phase, so that the introduction of the gaseous mixture comprising 130 kg of aniline and 177 kg of methanol could be continued at the original rate.

We claim:

1. In a process for the preparation of N,N-dimethylaniline by reacting an aniline with methanol in the gas phase at an elevated temperature and in a liquid phase catalyst, the improvement which comprises:

initially preparing said liquid phase catalyst before the reaction is commenced by eliminating water from orthophosphoric acid at a temperature of from 120° to 270° C. to obtain its anhydro acid which is then reacted with an arylamine selected from the group consisting of aniline and N,N-dimethylaniline to form the corresponding ammonium salt of said anhydro acid having a molar ratio of arylamine:phosphorus content of from 0.1:1 to 2:1; and subsequently passing a gaseous stream of aniline and methanol through said initially prepared liquid catalyst phase at a temperature of from 180° to 250° C.

2. A process as claimed in claim 1, wherein water is eliminated from the orthophosphoric acid at a temperature of from 160° to 230° C.

3. A process as claimed in claim 1, wherein the initially prepared liquid catalyst phase has a molar ratio of arylamine:phosphorus content of from 0.3:1 to 1.5:1.

4. A process as claimed in claim 3, wherein water is eliminated from the orthophosphoric acid at a temperature of from 200° to 210° C.

5. An improved continuous process for the preparation of N,N-dimethylaniline as carried out in claim 1, wherein the continuous reaction of gaseous aniline and methanol is occasionally interrupted and said liquid catalyst is treated with water or steam at a temperature of from 100° to 300° C. to regenerate the catalyst.

6. In a continuous process for the preparation of an N,N-dialkylarylamine by reacting an arylamine with an alcohol or a dialkyl ether in the presence of an oxygen acid of phosphorus or its ammonium salt as a liquid phase catalyst, the improvement for regenerating said catalyst which comprises occasionally interrupting the reaction and treating the liquid catalyst phase with water or steam at a temperature of from 100° to 300° C.

* * * * *

TABLE

| | Catalyst preparation | | Reaction parameters | | | Composition of the phase containing the crude product | | |
|---|---|---|---|---|---|---|---|---|
| Example | Arylamine (IV) | N:P molar ratio (*) | Pressure bar | Time h | DMA % | MMA % | Aniline % | o- and p-toluidines % |
| 1 | aniline | 0.7:1 | 1.4 | 36 | 97.7 | 1.9 | 0.1 | 0.3 |
| 2 | aniline | 1:1 | 1.3 | 30 | 98.6 | 1.0 | 0.1 | 0.3 |
| 3 | DMA | 0.33:1 | 1.3 | 15 | 98.2 | 1.3 | 0.1 | 0.4 |
| 4 | DMA | 0.5:1 | 1.3 | 15 | 98.5 | 1.0 | 0.1 | 0.4 |
| 5 | DMA | 1.25:1 | 1.3 | 10 | 98.7 | 0.8 | 0.1 | 0.4 |
| 6 | aniline | 1.25:1 | 1.2 | 50 | 55.0 DEA | 22.1 MEA | 20.0 | 3.0** |
| 7 | none | — | 1.3 | 15 | 97.2 | 2.1 | 0.1 | 0.6 |

*N:P - arylamine (IV):phosphorus content of the oxygen acid of phosphorus
DMA - N,N-dimethylaniline
MMA - N-monomethylaniline
DEA - N,N-diethylaniline
MEA - N-monoethylaniline
**o- and p-ethylanilines

UNITED STATES PATENT AND TRADEMARK OFFICE
CERTIFICATE OF CORRECTION

PATENT NO.  : 5,371,290
DATED       : December 6, 1994
INVENTOR(S) : Reuter et al.

It is certified that error appears in the above-identified patent and that said Letters Patent is hereby corrected as shown below:

On the title page: Item [54] and Column 1, line 1

Change "N,N-DIALKARYLAMINES" to --N,N-DIALKYLARYLAMINES--.

Signed and Sealed this

Twenty-first Day of February, 1995

Attest:

BRUCE LEHMAN

Attesting Officer

Commissioner of Patents and Trademarks